US012590161B2

(12) United States Patent
Yea et al.

(10) Patent No.: US 12,590,161 B2
(45) Date of Patent: Mar. 31, 2026

(54) ANTI-C-MPL ANTIBODY AND USE THEREOF

(71) Applicants: DAEGU GYEONGBUK INSTITUTE OF SCIENCE AND TECHNOLOGY, Daegu (KR); KOSIN UNIVERSITY INDUSTRY-ACADEMY COOPERATION, Busan (KR); INJE UNIVERSITY INDUSTRY-ACADEMIC COOPERATION FOUNDATION, Gimhae-si (KR)

(72) Inventors: Kyung Moo Yea, Daegu (KR); Jee-Yeong Jeong, Busan (KR); Sea Gwang Park, Busan (KR); Ji Won Shin, Busan (KR); Min-Jung Kim, Busan (KR)

(73) Assignees: DAEGU GYEONGBUK INSTITUTE OF SCIENCE AND TECHNOLOGY, Daegu (KR); KOSIN UNIVERSITY INDUSTRY-ACADEMY COOPERATION, Daegu (KR); INJE UNIVERSITY INDUSTRY-ACADEMIC COOPERATION FOUNDATION, Gimhae-si (KR)

( * ) Notice: Subject to any disclaimer, the term of this patent is extended or adjusted under 35 U.S.C. 154(b) by 530 days.

(21) Appl. No.: 18/038,497

(22) PCT Filed: Nov. 9, 2021

(86) PCT No.: PCT/KR2021/016252
§ 371 (c)(1),
(2) Date: May 24, 2023

(87) PCT Pub. No.: WO2022/114603
PCT Pub. Date: Jun. 2, 2022

(65) Prior Publication Data
US 2024/0010736 A1       Jan. 11, 2024

(30) Foreign Application Priority Data

Nov. 24, 2020   (KR) ........................ 10-2020-0158499
Oct. 20, 2021   (KR) ........................ 10-2021-0139827

(51) Int. Cl.
*C07K 16/28*       (2006.01)
*A61K 39/00*       (2006.01)
*A61P 7/06*        (2006.01)

(52) U.S. Cl.
CPC .......... *C07K 16/2866* (2013.01); *A61K 39/00* (2013.01); *A61P 7/06* (2018.01); *A61K 2039/505* (2013.01)

(58) Field of Classification Search
CPC ............ C07K 16/2866; C07K 2317/21; C07K 2317/52; C07K 2317/622; C07K 2317/70; C07K 2317/75; C07K 2319/00; A61K 39/00; A61K 2039/505; A61P 7/06
See application file for complete search history.

(56) References Cited

U.S. PATENT DOCUMENTS

2010/0298398 A1      11/2010   Gewirtz et al.

FOREIGN PATENT DOCUMENTS

| | | |
|---|---|---|
| EP | 2 006 380 | 12/2008 |
| EP | 2966088 | 1/2016 |
| KR | 10-2009-0021217 | 2/2009 |
| WO | 02-15926 | 2/2002 |
| WO | 2016-205784 | 12/2016 |

OTHER PUBLICATIONS

Jing et al, Thrombosis Research, 170, 200-206, 2018 (Year: 2018).*
Caizheng Li et al., "The pharmacology and clinical application of thrombopoietin receptor agonists", International Journal of Hematology, vol. 100, No. 6, Sep. 18, 2014, pp. 529-539.
Akihito Fujimi et al., "Identification of anti-thrombopoietin receptor antibody in prolonged thrombocytopenia after allogeneic hematopoietic stem cell transplantation treated successfully with eltrombopag", International Journal of Hematology, vol. 102, No. 4, May 13, 2015, pp. 471-476.

* cited by examiner

*Primary Examiner* — Nelson B Moseley, II
*Assistant Examiner* — Josephine K Darpolor
(74) *Attorney, Agent, or Firm* — LEX IP MEISTER, PLLC

(57) ABSTRACT

The present invention relates to a novel anti-C-MPL antibody and a use thereof, and specifically, to an anti-C-MPL antibody having an effect of increasing platelet production and its number through the maturation of megakaryocytes in the bone marrow, and a use thereof. The novel anti-C-MPL antibody (2R13) of the present invention is a polymer material and has a longer half-life than the conventional therapeutic agents, and it has the advantage of low self-antibody production and low immunogenicity as an antibody agent. In addition, it can be used as a therapeutic agent for thrombocytopenia by increasing the platelet level of patients suffering from chronic or complication-induced immune thrombocytopenia.

4 Claims, 10 Drawing Sheets
Specification includes a Sequence Listing.

[FIG. 1]
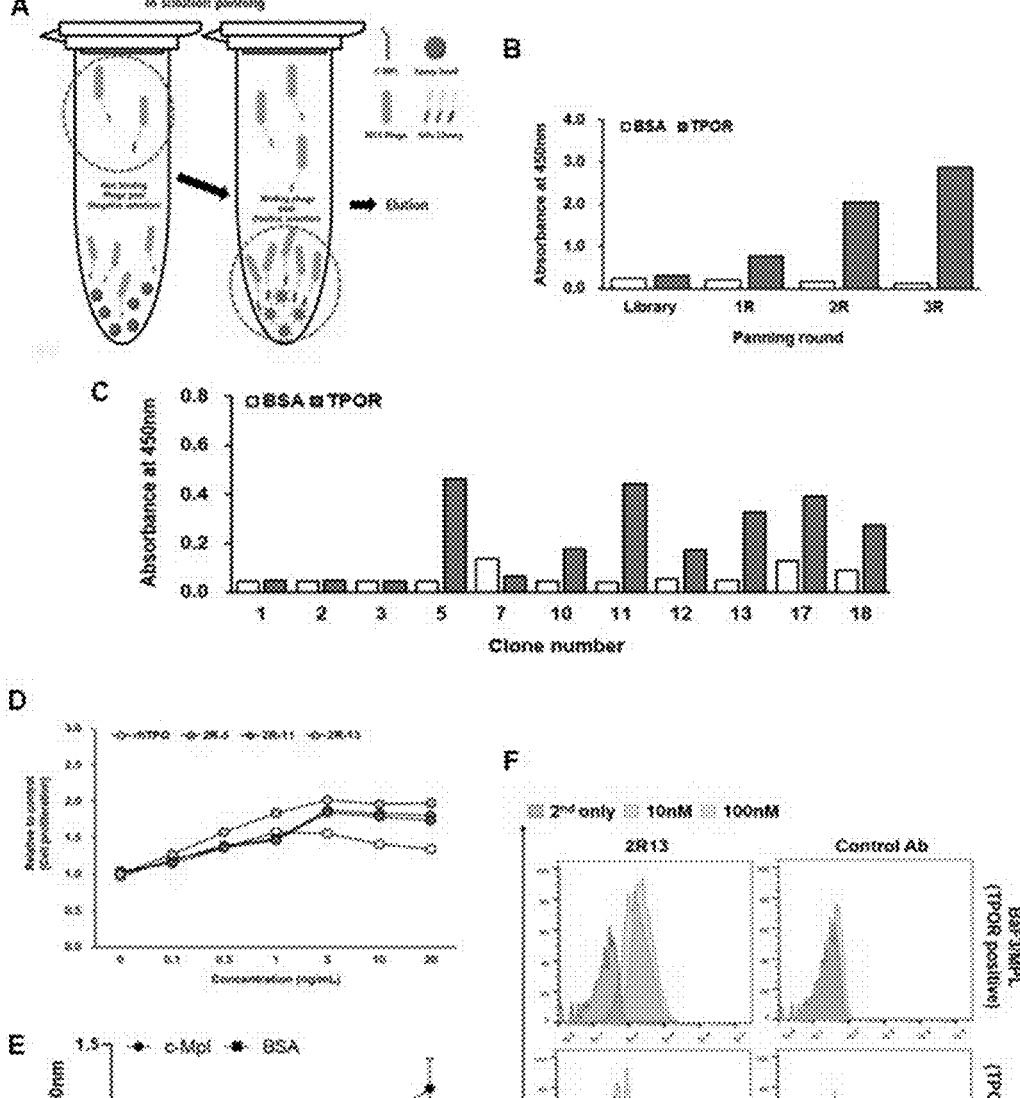

[FIG. 2]
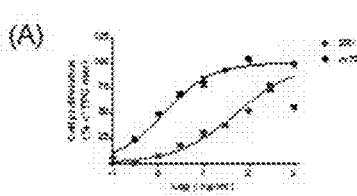
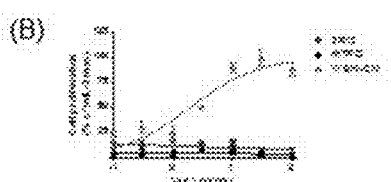
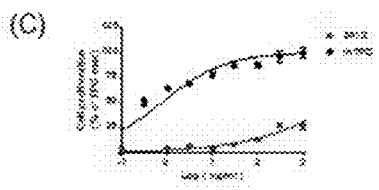
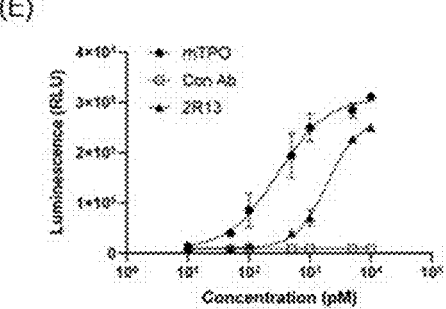
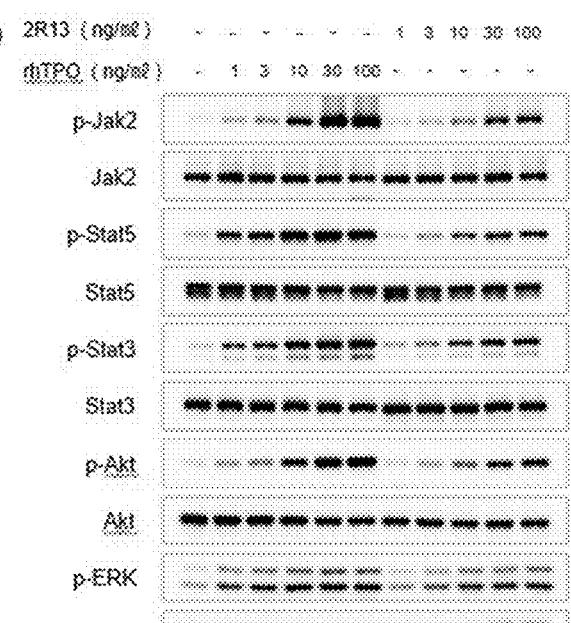

[FIG. 3]
(A)
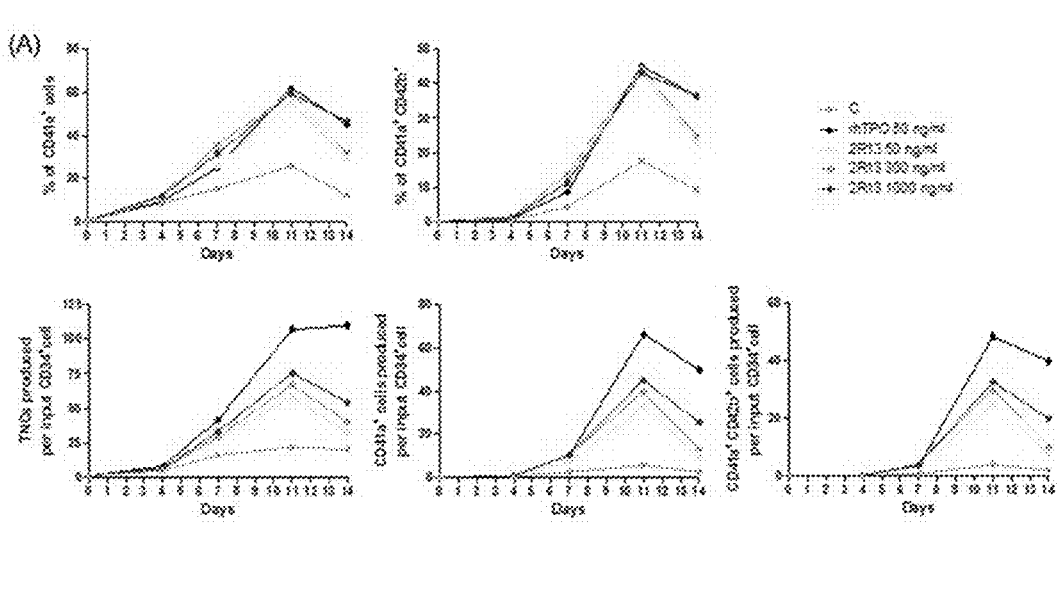
(B)
(C)
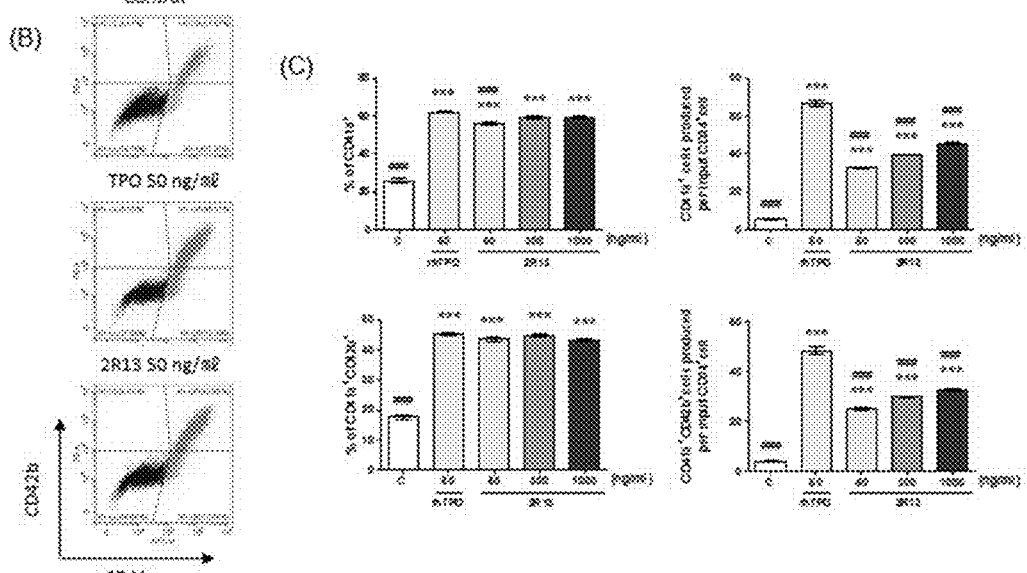

[FIG. 4]
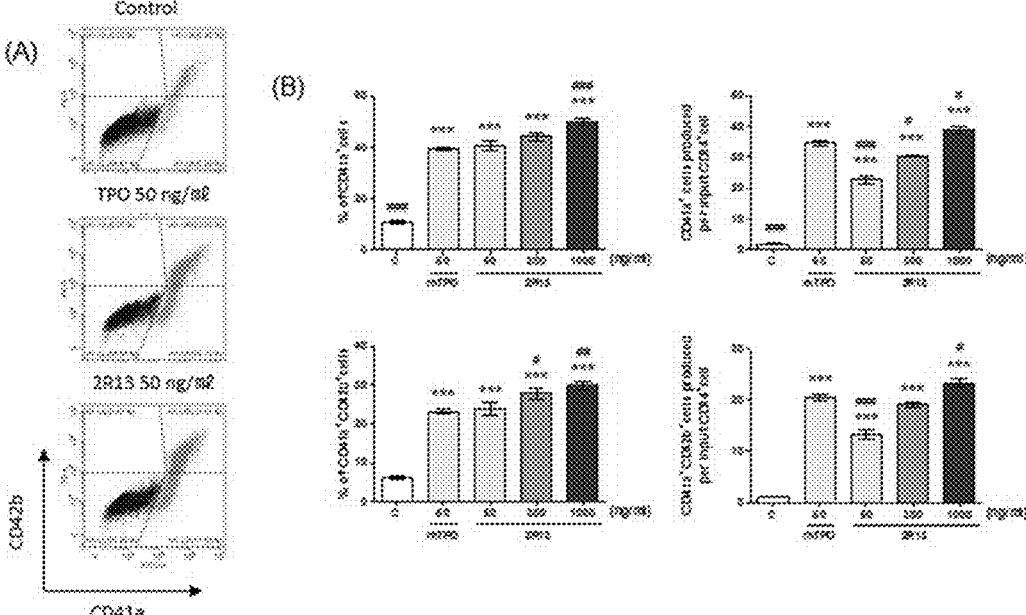
[FIG. 5]
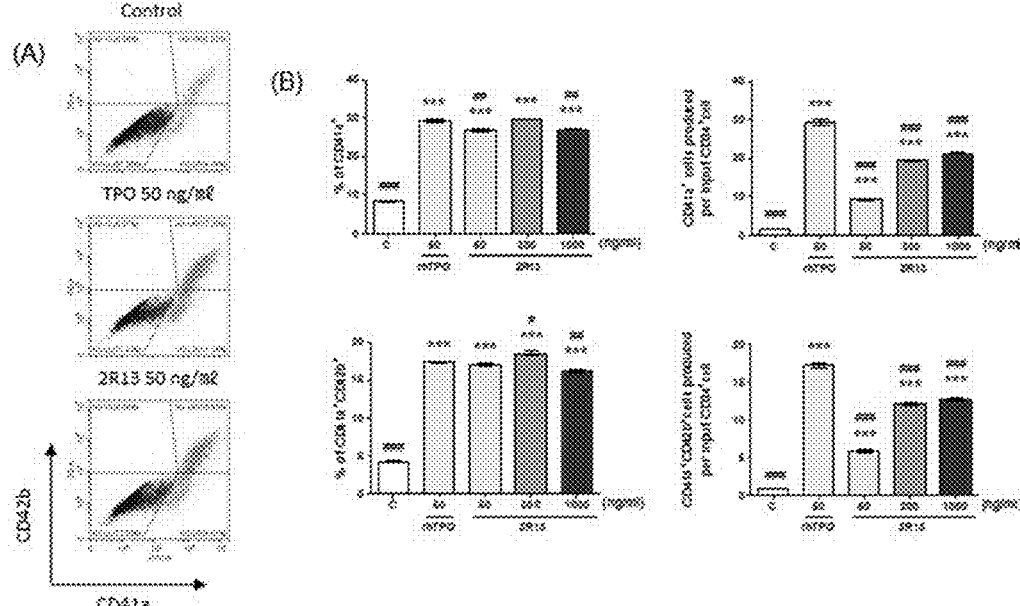

[FIG. 6]
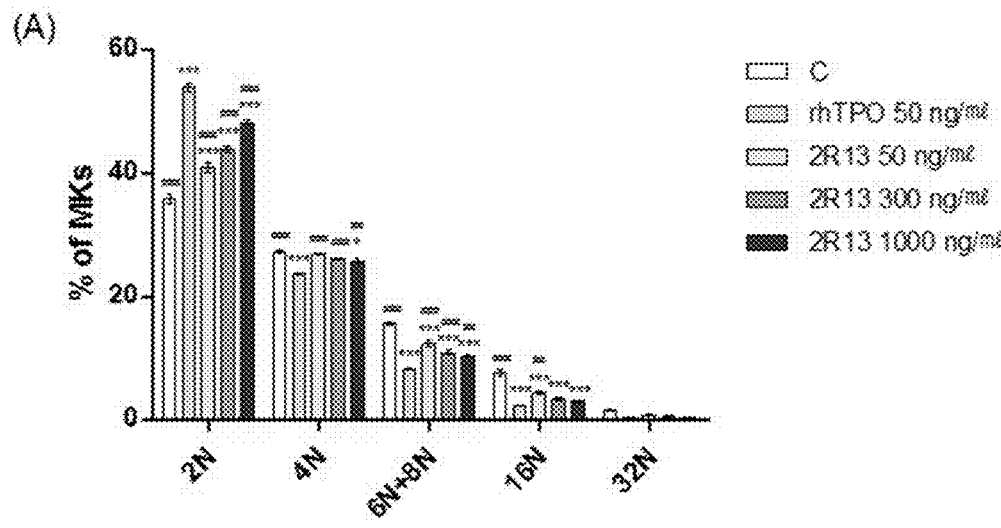
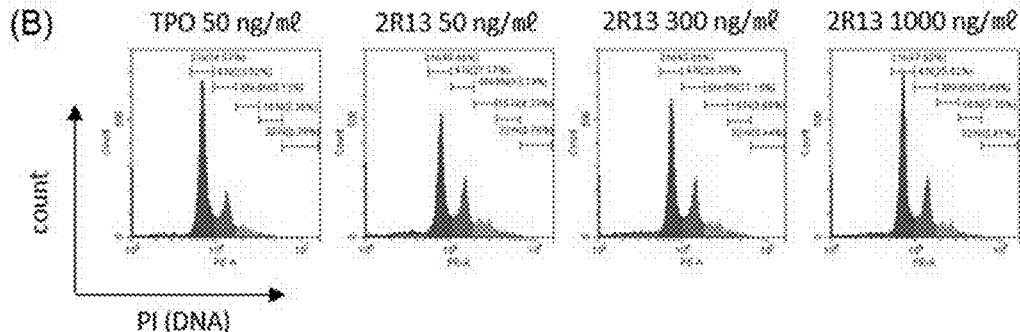
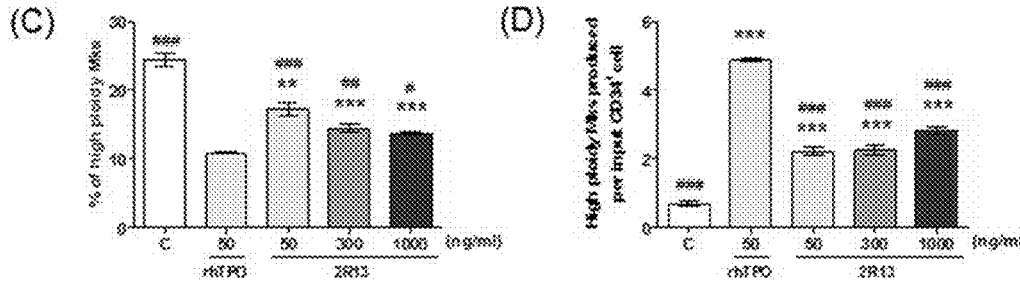

[FIG. 7]
(A)
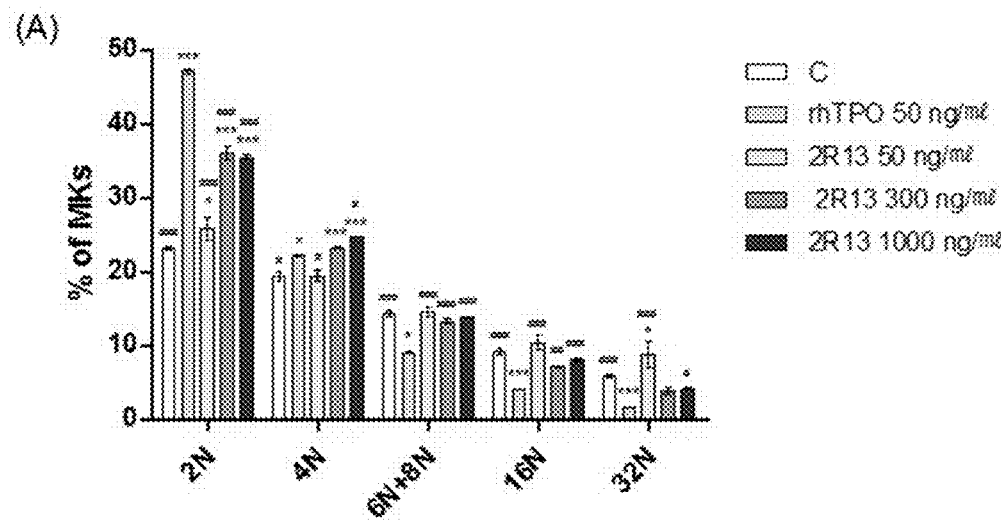
(B)
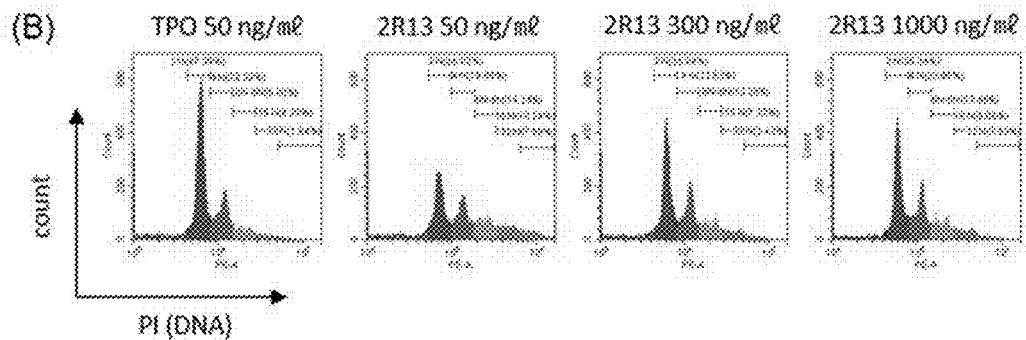
(C)                 (D)
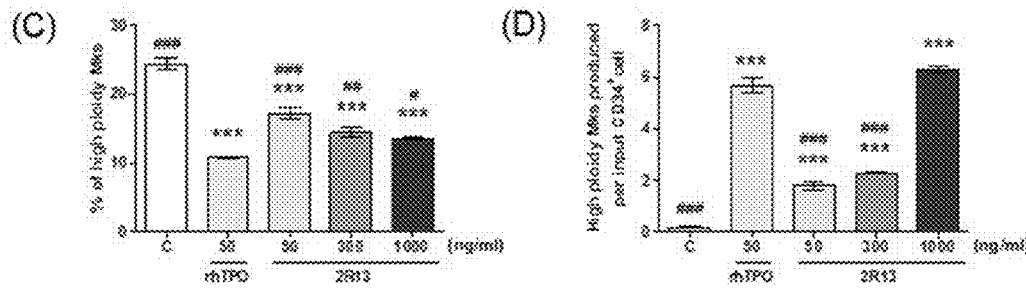

[FIG. 8]
(A)
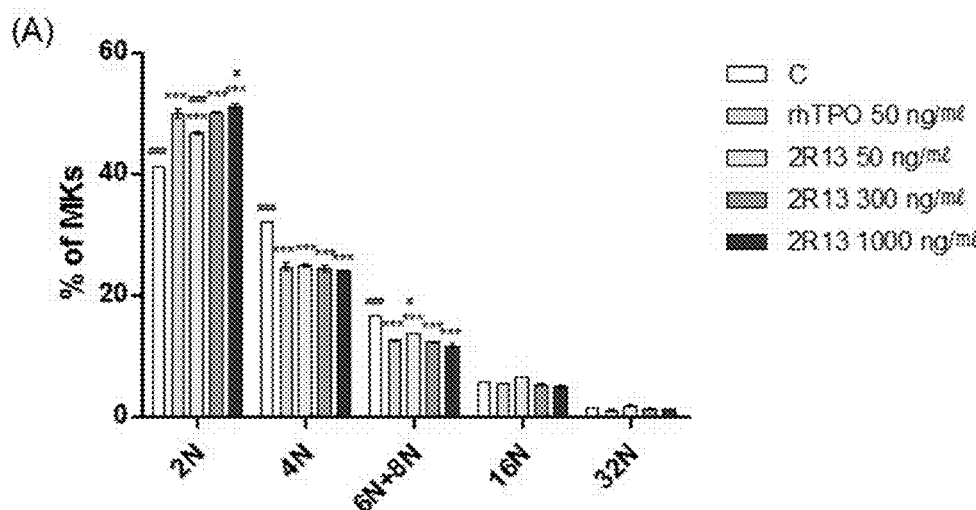
□ C
▨ rhTPO 50 ng/mℓ
□ 2R13 50 ng/mℓ
▨ 2R13 300 ng/mℓ
■ 2R13 1000 ng/mℓ
(B)
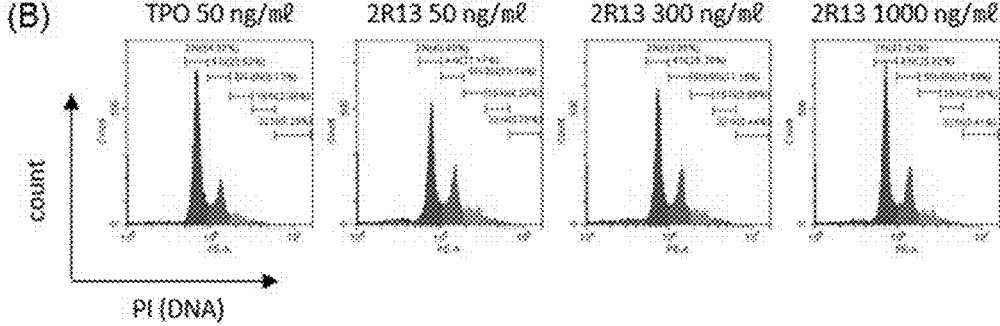
TPO 50 ng/mℓ    2R13 50 ng/mℓ    2R13 300 ng/mℓ    2R13 1000 ng/mℓ
(C)               (D)
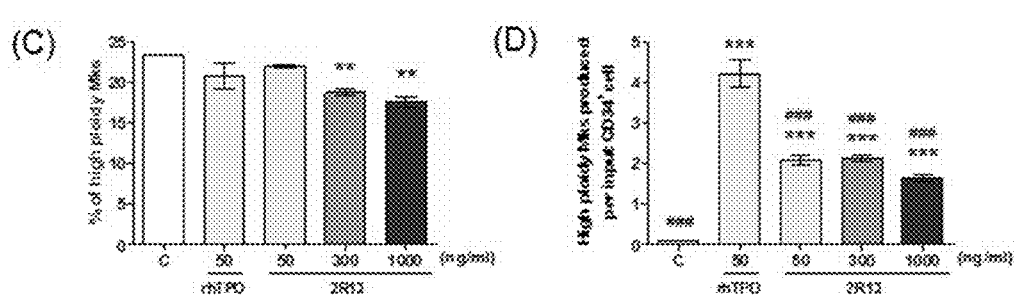

[FIG. 9]
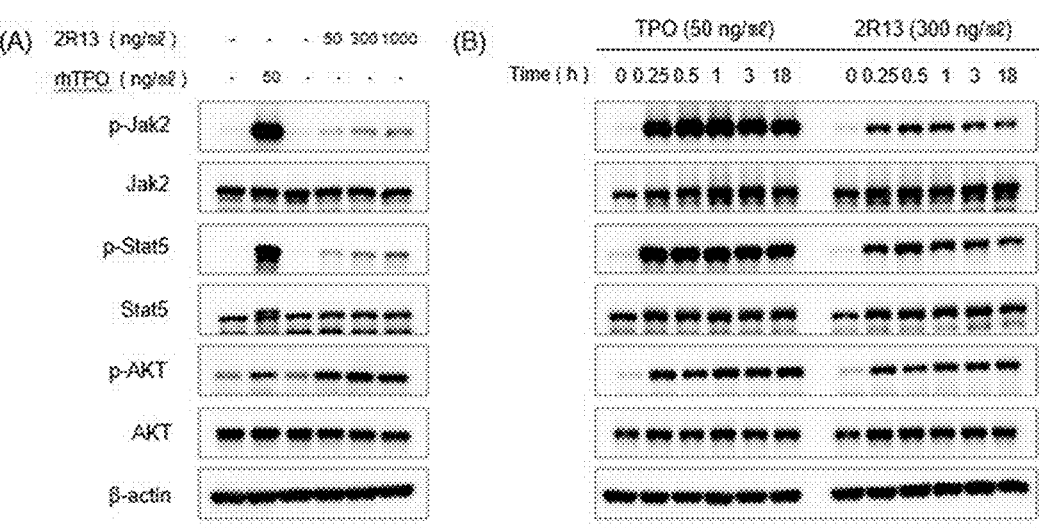

[FIG. 10]
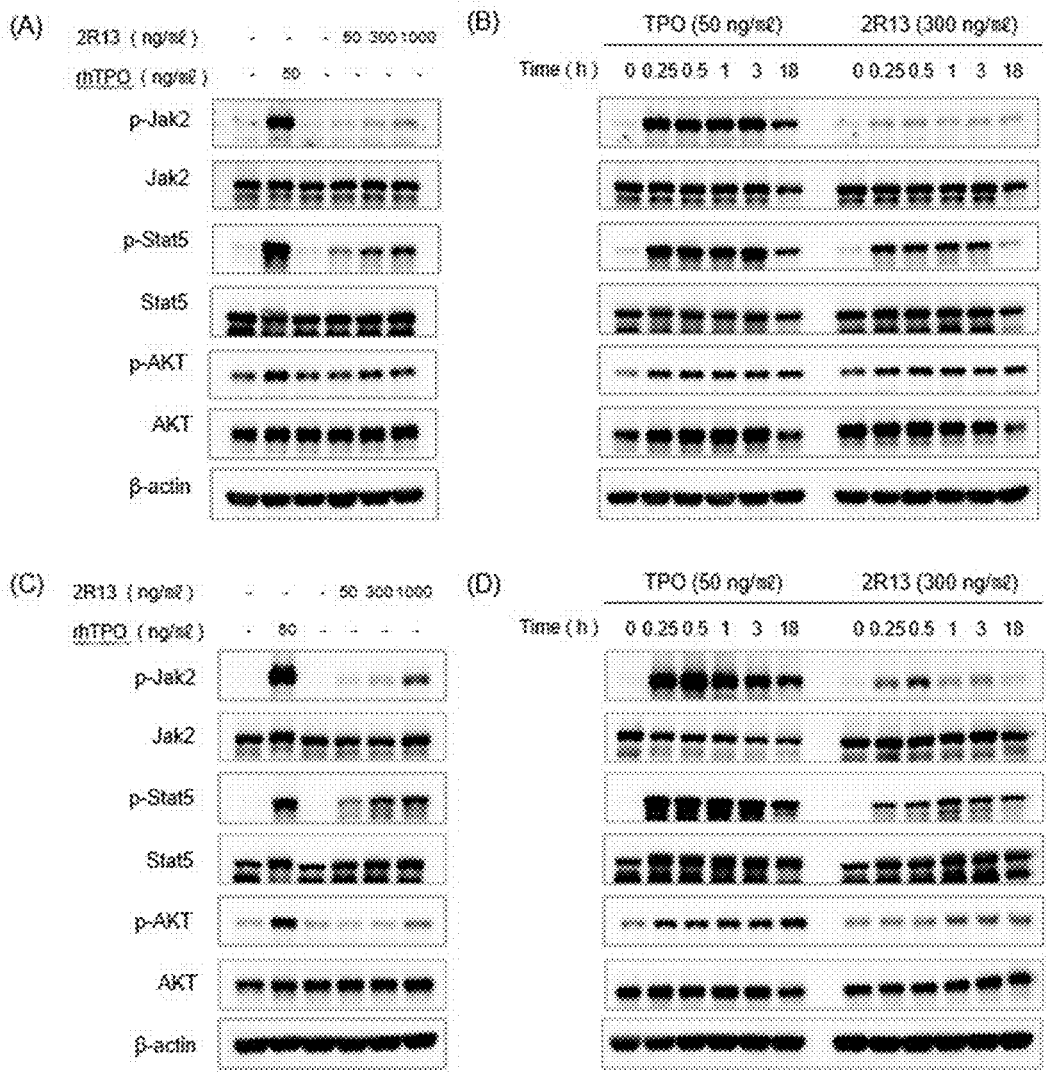

[FIG. 11]
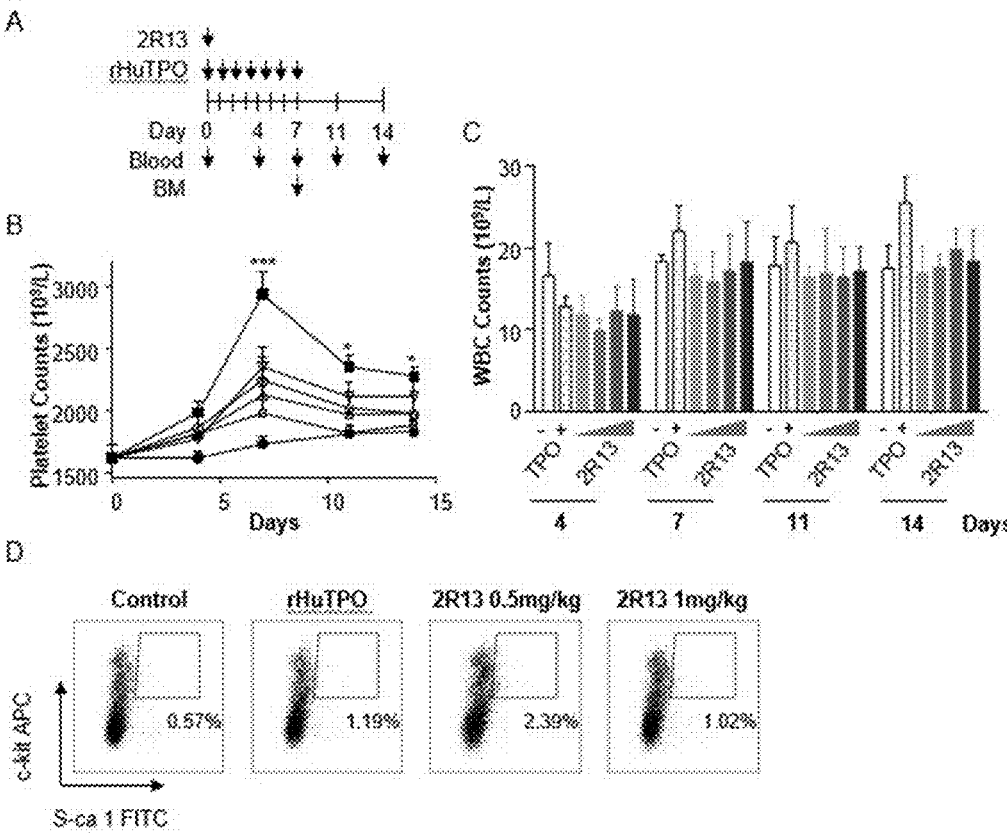
[FIG. 12]
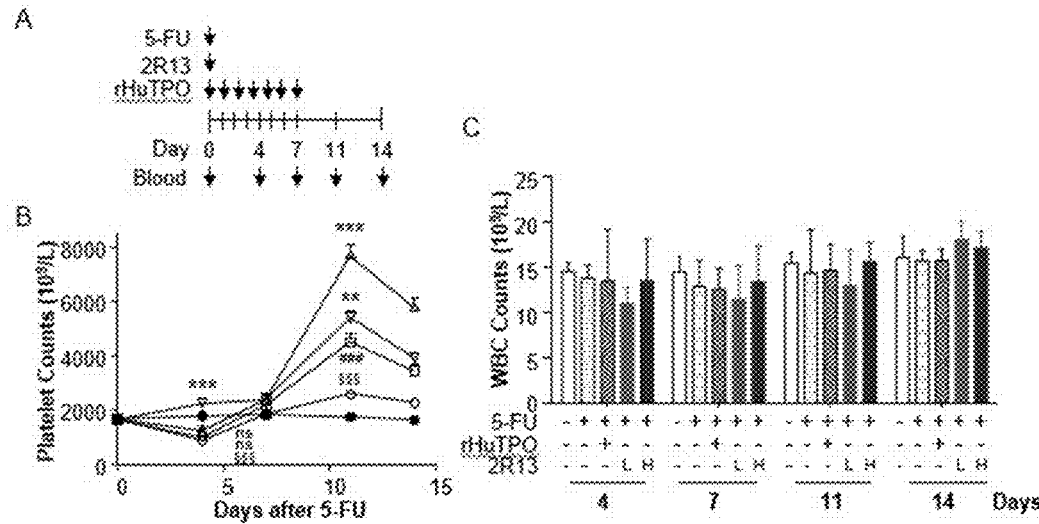

SEQUENCE LISTING

```
<160> NUMBER OF SEQ ID NOS: 6

<210> SEQ ID NO 1
<211> LENGTH: 8
<212> TYPE: PRT
<213> ORGANISM: Artificial Sequence
<220> FEATURE:
<223> OTHER INFORMATION: VH CDR1

<400> SEQUENCE: 1

Arg Asp Thr Phe Asn Thr Tyr Gly
1               5

<210> SEQ ID NO 2
<211> LENGTH: 8
<212> TYPE: PRT
<213> ORGANISM: Artificial Sequence
<220> FEATURE:
<223> OTHER INFORMATION: VH CDR2

<400> SEQUENCE: 2

Ile Ile Pro Ile Phe Gly Thr Ala
1               5

<210> SEQ ID NO 3
<211> LENGTH: 11
<212> TYPE: PRT
<213> ORGANISM: Artificial Sequence
<220> FEATURE:
<223> OTHER INFORMATION: VH CDR3

<400> SEQUENCE: 3

Ala Arg Asp Arg Arg Ala Gly Gly Tyr Asp Tyr
1               5                   10

<210> SEQ ID NO 4
<211> LENGTH: 6
<212> TYPE: PRT
<213> ORGANISM: Artificial Sequence
<220> FEATURE:
<223> OTHER INFORMATION: VL CDR1

<400> SEQUENCE: 4

Gln Gly Leu Gly Arg Trp
1               5

<210> SEQ ID NO 5
<211> LENGTH: 3
<212> TYPE: PRT
<213> ORGANISM: Artificial Sequence
<220> FEATURE:
<223> OTHER INFORMATION: VL CDR2
```

-continued

```
<400> SEQUENCE: 5

Ala Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: VL CDR3

<400> SEQUENCE: 6

Gln Gln Ser Asn Ser Phe Pro Trp Thr
1               5
```

ANTI-C-MPL ANTIBODY AND USE THEREOF

TECHNICAL FIELD

The present invention relates to a novel anti-C-MPL antibody and a use thereof, and specifically, to an anti-C-MPL antibody having an effect of increasing the number of platelets due to an increase in platelet production through the maturation of megakaryocytes in the bone marrow and uses thereof.

BACKGROUND ART

Immune thrombocytopenia (ITP) is characterized by low platelet counts (separated peripheral platelets less than $100\times 10^9$ L) due to accelerated platelet destruction and impaired platelet production. Pathogenic autoreactive antibodies, T cells directed against platelet antigens, cytokine imbalance, and the microenvironment of the bone marrow niche contribute to reduced peripheral platelet counts, often leading to chronic disease. About 18% of patients with ITP are asymptomatic, but active bleeding is a major risk factor in patients with ITP and can show a variety of symptoms, such as petechiae including epistaxis, purpura, mucosal bleeding in the urinary tract, and bleeding in the gastrointestinal tract or mouth. Therefore, restoring a durable platelet count capable of sufficient hemostasis has become a major treatment strategy for patients with ITP.

Physiological formation of blood clots is regulated at several stages by various cytokines, the most important of which is thrombopoietin (TPO). TPO determines megakaryocyte lineage in HSCs and stimulates the maturation of megakaryocytes in the bone marrow niche through the TPO receptor, c-MPL. This process is regulated by plasma TPO levels through a negative feedback loop accompanying binding to and removal of TPO by circulating platelets. Thus, a reduced platelet count increases circulating TPO levels, which in turn promotes megakaryocyte production to normalize platelet counts. Indeed, elevated TPO levels have been shown in patients with secondary-induced thrombocytopenia caused by aplastic anemia. However, there were no significant changes in TPO levels and platelet turnover in ITP patients. Rather, platelets with normal or reduced TPO levels and shorter survival times were observed when compared to healthy subjects. In addition, although the number of megakaryocytes was increased in some patients, these megakaryocytes were often immature or showed morphological abnormalities, and caspase-3 was activated, resulting in reduced platelet productivity. These clinical results have led to the development of therapeutics that mimic endogenous TPO to reach homeostasis.

To date, the TPO mimetics (TPO-RA) approved by the FDA for the remedy of ITP are Romiplostim, Eltrombopag, and Avatrombopag. While Romiplostim is a peptibody that acts on extracellular molecules, the other two are non-peptide molecules that bind to the transmembrane domain, and clinical trials have already demonstrated the efficacy and tolerability of these agents for platelet production and hemostasis. Nevertheless, in a series of primary ITP adult patients treated with Romiplostim, 59.5% of subjects showed a loss of response due to unwanted neutralizing antibodies without cross-reactivity with endogenous TPO, and Eltrombopag was reported as nonspecific. These agents act as potent iron chelators, resulting in anti-proliferative effects in leukemia cell lines and rarely cause iron deficiency in some patients. Also, relatively frequent side effects such as dietary restrictions and hepatotoxicity have been described. Avatrombopag was approved by the FDA in 2018 as an alternative to the lack of the conventional remedy. This solved the problem of the conventional medicines (Romiplostim, Avatrombopag), but required daily administration frequency. Avatrombopag and its metabolites of 88% are mainly excreted in feces, of which 34% are excreted unmetabolized. These results indicate a need to develop longer lasting and more effective therapies.

Despite previous attempts to establish TPO agonist minibodies, Fabs, and domain subclasses converted TPO agonist antibodies, clinical studies of antibody-based TPO agonists have not yet been reported. In the present invention, the present inventors have developed a TPO receptor agonist antibody. They constructed this agonist ab to stimulate megakaryogenesis and platelet activation in human primary cells, and at the same time, it was demonstrated that the platelet count was restored in the thrombocytopenia-induced mouse model, and the biological function of the natural ligand TPO was replicated. From a therapeutic point of view, the present invention can be provided as an excellent TPO mimetic that ensures extended half-life and efficacy and clinical safety.

DISCLOSURE

Technical Problem

An object of the present invention is to provide a novel anti-c-MPL antibody or antigen-binding fragment thereof.

Another object of the present invention is to provide a nucleic acid molecule encoding the anti-c-MPL antibody or antigen-binding fragment thereof, a recombinant expression vector comprising the nucleic acid molecule, and cells transformed with the recombinant expression vector.

Another object of the present invention is to provide a composition for preventing, improving or treating thrombocytopenia comprising the anti-c-MPL antibody or antigen-binding fragment thereof as an active ingredient.

Technical Solution

In order to achieve the above object, the present invention provides an anti-c-MPL antibody or antigen-binding fragment thereof, comprising: a heavy chain variable region comprising a heavy chain CDR1 composed of amino acid sequence represented by SEQ ID NO: 1, a heavy chain CDR2 composed of amino acid sequence represented by SEQ ID NO: 2, and a heavy chain CDR3 composed of amino acid sequence represented by SEQ ID NO: 3; and a light chain variable region comprising a light chain CDR1 composed of amino acid sequence represented by SEQ ID NO: 4, a light chain CDR2 composed of amino acid sequence represented by SEQ ID NO: 5, and a light chain CDR3 composed of amino acid sequence represented by SEQ ID NO: 6.

The present invention also provides a nucleic acid molecule encoding the anti-c-MPL antibody or antigen-binding fragment thereof.

In addition, the present invention provides a recombinant expression vector containing the nucleic acid molecule.

In addition, the present invention provides a cell transformed with the recombinant expression vector.

Furthermore, the present invention provides a pharmaceutical composition for preventing or treating thrombocytopenia comprising the anti-c-MPL antibody or antigen-binding fragment thereof as an active ingredient.

Furthermore, the present invention provides a health functional food composition for preventing or improving thrombocytopenia comprising the anti-c-MPL antibody or antigen-binding fragment thereof as an active ingredient.

Advantageous Effects

The present invention relates to a novel anti-c-MPL antibody and a use thereof, and specifically, to an anti-c-MPL antibody having an effect of increasing the number of platelets due to an increase in platelet production through the maturation of megakaryocytes in the bone marrow and uses thereof. The novel anti-C-MPL antibody (2R13) of the present invention is a polymer material and has a longer half-life than conventional therapeutic agents, and it has the advantage of low self-antibody production and low immunogenicity, as an antibody agent. In addition, it can be used as a therapeutic agent for thrombocytopenia by increasing the platelet level of patients suffering from chronic or complication-induced immune thrombocytopenia.

DESCRIPTION OF DRAWINGS

FIG. 1 shows that 2R13, a functional scFv-Fc antibody, specifically binds to TPOR.

FIG. 2 shows that 2R13 promotes cell growth and stimulates the JAK/STAT signaling pathway in BaF3/MPL cells.

FIG. 3 to FIG. 5 show that 2R13 induces megakaryocytic differentiation of PB CD34+ cells.

FIG. 6 to FIG. 8 show that 2R13 induces highly ploidy megakaryocytic differentiation from PB-CD34+ cells.

FIG. 9 and FIG. 10 show that 2R13 stimulates the TPOR signaling pathway in human platelets.

FIG. 11 shows the effect of 2R13 on platelets and WBCs and the induction potential of HSPC in a WT mouse model.

FIG. 12 shows the effect of 2R13 on platelets and WBCs in a thrombocytopenia model.

BEST MODE

The present invention provides an anti-c-MPL antibody or antigen-binding fragment thereof, comprising: a heavy chain variable region comprising a heavy chain CDR1 composed of amino acid sequence represented by SEQ ID NO: 1, a heavy chain CDR2 composed of amino acid sequence represented by SEQ ID NO: 2, and a heavy chain CDR3 composed of amino acid sequence represented by SEQ ID NO: 3; and a light chain variable region comprising a light chain CDR1 composed of amino acid sequence represented by SEQ ID NO: 4, a light chain CDR2 composed of amino acid sequence represented by SEQ ID NO: 5, and a light chain CDR3 composed of amino acid sequence represented by SEQ ID NO: 6.

On the other hand, CDRs consisting of amino acids represented by SEQ ID NO: 1 to SEQ ID NO: 6 are listed in Table 1 below.

TABLE 1

| Antibody 2R13 CDR sequence | | | |
|---|---|---|---|
| VH CDR Seq. | CDR1 | RDTFNTYG | SEQ ID NO: 1 |
| | CDR2 | IIPIFGTA | SEQ ID NO: 2 |
| | CDR3 | ARDRRAGG YDY | SEQ ID NO: 3 |

TABLE 1-continued

| Antibody 2R13 CDR sequence | | | |
|---|---|---|---|
| VL CDR Seq. | CDR1 | QGLGRW | SEQ ID NO: 4 |
| | CDR2 | AAS | SEQ ID NO: 5 |
| | CDR3 | QQSNSFPWT | SEQ ID NO: 6 |

As used herein, the term "antibody" refers to a protein molecule that acts as a receptor that specifically recognizes an antigen, including an immunoglobulin molecule that is immunologically reactive with a specific antigen, and includes, for example, monoclonal antibodies, polyclonal antibodies, full-length antibodies and antibody fragments. Also, the term "antibody" may include bivalent or bispecific molecules (e.g., bispecific antibodies), diabodies, triabodies or tetrabodies.

As used herein, the term "monoclonal antibody" refers to an antibody molecule of a single molecular composition obtained from substantially the same antibody population, and such a monoclonal antibody, unlike polyclonal antibodies that can bind to several epitopes, shows single binding and affinity for a specific epitope. In the present invention, the term "full-length antibody" has a structure having two full-length light chains and two full-length heavy chains, and each light chain is connected to the heavy chain by a disulfide bond. The constant region of the heavy chain has gamma (γ), mu (μ), alpha (α), delta (δ), and epsilon (ε) types, and subclasses thereof include gamma 1 (γ1), gamma 2 (γ2), and gamma 3 (γ3), gamma 4 (γ4), alpha 1 (α1) and alpha 2 (α2). The constant region of the light chain has kappa (κ) and lambda (λ) types. IgG is a subtype and includes IgG1, IgG2, IgG3 and IgG4.

As used herein, the term "heavy chain" refers to a full-length heavy chain and fragments thereof comprising a variable region VH and three constant regions CH1, CH2 and CH3 comprising an amino acid sequence having sufficient variable region sequence to impart specificity to an antigen. In addition, as used herein, the term "light chain" may include both a full-length light chain and fragments thereof comprising a variable region VL and a constant region CL, which include an amino acid sequence having sufficient variable region sequence to impart specificity to an antigen.

As used herein, the terms "fragment", "antibody fragment" and "antigen-binding fragment" are used interchangeably to refer to any fragment of an antibody of the present invention that has the antigen-binding function of the antibody. Exemplary antigen-binding fragments include, but are not limited to, Fab, Fab', F(ab')2 and Fv, and the like.

As used herein, the term "CDR" refers to a region that binds to an antigen as a hypervariable region, which is a region having a different amino acid sequence for each antibody in the heavy and light chain variable regions of an antibody.

Antibodies or antigen-binding fragments thereof of the present invention may include not only the sequences of the antibodies described herein, but also biological equivalents thereof to the extent that they can exhibit the ability to specifically bind to c-MPL. For example, the amino acid sequence of an antibody may be further modified to further improve its binding affinity and/or other biological properties. Such modifications include, for example, deletions, insertions and/or substitutions of residues in the amino acid sequence of the antibody. Such amino acid variations are made based on the relative similarity of amino acid side chain substituents, such as hydrophobicity, hydrophilicity, charge, size, etc. Analysis of the size, shape and type of amino acid side chain substituents revealed that arginine, lysine and histidine are all positively charged residues; alanine, glycine and serine have similar sizes; and phenylalanine, tryptophan and tyrosine have similar shapes. Therefore, on the basis of this, arginine, lysine and histidine; alanine, glycine and serine; and phenylalanine, tryptophan and tyrosine are biologically functional equivalents.

The present invention also provides a nucleic acid molecule encoding the anti-c-MPL antibody or antigen-binding fragment thereof.

As used herein, the term "nucleic acid molecule" has a meaning comprehensively including DNA (gDNA and cDNA) and RNA molecules, and nucleotides, which are basic structural units in nucleic acid molecules, include not only natural nucleotides, but also analogs in which sugar or base sites are modified. The sequences of the nucleic acid molecules encoding the heavy and light chain variable regions of the present invention may be modified, and the modifications include nucleotide insertions, deletions, or non-conservative or conservative substitutions.

In addition, the present invention provides a recombinant expression vector comprising the nucleic acid molecule.

In the present invention, "vector" refers to a self-replicating DNA molecule used to carry clonal genes (or other fragments of clonal DNA).

In the present invention, "expression vector" refers to a recombinant DNA molecule containing a desired coding sequence and an appropriate nucleic acid sequence essential for expressing the operably linked coding sequence in a specific host organism. Expression vectors may preferably include one or more selectable markers. The marker is a nucleic acid sequence having a characteristic that can be selected by a conventional chemical method, and includes all genes capable of distinguishing transformed cells from non-transformed cells. Examples include genes for resistance to antibiotics such as Ampicillin, Kanamycin, Geneticin (G418), Bleomycin, Hygromycin, and Chloramphenicol, but it is not limited thereto and can be selected suitably by those skilled in the art.

In order to express the DNA sequence of the present invention, any of a wide variety of expression regulatory sequences can be used in the vector. Examples of useful expression regulatory sequences may include, for example, early and late promoters of SV40 or adenovirus, promoters and enhancers of CMV, LTR of retroviruses, lac system, trp system, TAC or TRC system, T3 and T7 promoters, main operator and promoter region of phage lambda, the regulatory region of the fd code protein, the promoter for 3-phosphoglycerate kinase or other glycolase, the promoters of the phosphatase such as Pho5, alpha-crossing system promoters of yeast and constructs and other induced sequences known to regulate the expression of genes of prokaryotic or eukaryotic cells or their viruses, and various combinations thereof.

The vector expressing the antibody of the present invention may be a vector system in which the light and heavy chains are simultaneously expressed in one vector, or a system in which the light and heavy chains are respectively expressed in separate vectors. In the latter case, both vectors are introduced into the host cell through co-transformation and targeted transformation. The co-transformation is a method of screening cells expressing both light and heavy chains after simultaneously introducing each vector DNA encoding light and heavy chains into a host cell. The targeted transformation is a method of selecting cells transformed with a vector containing a light chain (or heavy chain) and again transforming the selected cells expressing the light chain with a vector containing a heavy chain (or light chain) to express both the light and heavy chains, and thereby finally selecting cells.

In addition, the present invention provides cells transformed with the recombinant expression vector.

Cells capable of continuously cloning and expressing the vector of the present invention stably may be any host cell known in the art, may include prokaryotic host cells, for example, *Escherichia coli, Bacillus* strains such as *Bacillus subtilis* and *Bacillus thuringiensis, Streptomyces, Pseudomonas* (e.g. *Pseudomonas putida*), *Proteus mirabilis* or *Staphylococcus* (e.g. *Staphylococcus carnosus*), but they are not limited thereto.

In the method of preparing the antibody or antigen-binding fragment thereof, the culture of transformed cells may be performed according to a suitable medium and culture conditions known in the art. Such a culture process can be performed by easily adjusting according to the selected strain by those skilled in the art. The cell culture is divided into a suspension culture and an adhesion culture according to the cell growth way and it is divided into batch, fed-batch and continuous culture methods depending on the culture method. The medium used for culture must adequately satisfy the requirements of a particular strain.

In addition, the present invention provides a pharmaceutical composition for preventing or treating thrombocytopenia comprising the anti-c-MPL antibody or antigen-binding fragment thereof as an active ingredient.

Specifically, the pharmaceutical composition can induce megakaryocytic generation, platelet activation, and platelet count increase.

The pharmaceutical composition of the present invention may further include a pharmaceutically acceptable carrier, and the pharmaceutically acceptable carrier is commonly used in the preparation and may include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, stearic acid, magnesium and mineral oil, and the like, but it is not limited thereto. The pharmaceutical composition of the present invention may further include a lubricant, a wetting agent, a sweetener, a flavoring agent, an emulsifying agent, a suspending agent, a preservative, etc. in addition to the above components.

The pharmaceutical composition of the present invention can be administered orally or parenterally, and for parenteral administration, it can be administered by intravenous injection, subcutaneous injection, intramuscular injection, intraperitoneal injection, endothelial administration, topical administration, intranasal administration, intrapulmonary administration, rectal administration, etc. When administered orally, the protein or peptide is digested, so the composition for oral administration can be formulated to coat the active agent or to protect it from the degradation in the stomach, and the composition of the present invention can be administered by any device capable of transporting the active substance to target cells.

Suitable dosages of the pharmaceutical composition of the invention varies according to factors such as formulation method, mode of administration, patient's age, weight, sex, morbid condition, food, time of administration, route of administration, rate of excretion and response sensitivity, and usually, an experienced physician can easily determine and prescribe a dose effective for the desired treatment or prevention.

The pharmaceutical composition of the present invention is prepared in a unit dosage form by formulating using a pharmaceutically acceptable carrier and/or excipient or by incorporating it into a multi-dose container, according to a method that can be easily carried out by a person skilled in the art to which the present invention pertains. At this time, the formulation may be in the form of a solution, suspension, or emulsion in an oil or aqueous medium, or may be in the form of extract, powder, suppository, powder, granule, tablet or capsule, and may further include a dispersant or stabilizer.

In addition, the present invention provides a health functional food composition for preventing or improving thrombocytopenia comprising the anti-c-MPL antibody or antigen-binding fragment thereof as an active ingredient.

The health functional food composition may be provided in the form of a powder, granule, tablet, capsule, syrup, beverage or pill, and the health food composition is used in combination with other food or food additives other than the composition according to the present invention as an active ingredient, and it can be suitably used according to the conventional method. The mixed amount of the active ingredient can be appropriately determined according to its purpose of use, for example, prevention, health or therapeutic treatment.

The effective dose of the antibody or antigen-binding fragments thereof contained in the health functional food composition can be used in accordance with the effective dose of the pharmaceutical composition, but it may be the above range and less than in the case of the long-term intake for health and hygiene purposes or for health control purposes and it is clear that the active ingredient can be used in an amount of at least the above range because there is no problem in terms of safety.

There is no particular limitation regarding the kind of the health functional food, and examples thereof include meat, sausage, bread, chocolate, candies, snacks, confectionery, pizza, ramen, other noodles, gums, dairy products including ice cream, various soups, beverages, tea, drinks, alcoholic beverages and vitamins complex, etc.

Hereinafter, the present invention will be described in more detail through examples. These examples are only intended to illustrate the present invention in more detail, and it will be apparent to those skilled in the art that the scope of the present invention is not limited by these examples according to the gist of the present invention. The examples of the present invention are provided to more completely explain the present invention to those of ordinary skill in the art.

Experimental Example

The following experimental examples are intended to provide experimental examples commonly applied to each example according to the present invention.

1. Cell Lines and Cell Culture

Murine pre-B cell line BaF3 cells obtained from Arthur J. Sykowski (Beth Israel Deaconedd Medical Center, Boston, MA) were cultured in 10% fetal bovine serum (FBS) and 5% WEHI-3B cell conditioned medium (WEHI-CM, i.e. interleukin-3 (source of IL-3)) in RPMI-1640 (Lonza). To establish a BaF3/MPL cell line expressing the human thrombopoietin receptor (hTPOR, genetic name MPL), BaF3 cells were stably transfected with the pCMV-hMPL plasmid (Origene). Surface expression of hTPOR was confirmed by flow cytometry using CD110-APC (Miltenyi Biotech). The acute megakaryoblastic leukemia cell line MO7e was purchased from the DSMZ (German Collection of Microorganisms and Cell Cultures) and maintained in Iscove's Modified Dulbecco's Medium (IMDM) supplemented with 10% FBS and 10 ng/mL IL-3. Normal human platelets with an expiration date of 1 to 2 days were collected from the Kosin University Gospel Hospital (KUGH) blood bank. The present study using human derived samples (platelets and peripheral blood, PB) was approved by the Institutional Review Board of KUGH.

2. Cell Proliferation Assay

To determine the activity of the TPOR agonists, cell proliferation assays were performed using $1 \times 10^4$ cells/ml for BaF3/MPL or $5 \times 10^5$ cells/ml for Mo7e. BaF3/MPL cells in RPMI with 10% FBS and MO7e cells in IMDM with 10% FBS (without IL-3 supplementation) were cultured for 48 hours in 96-well plates in the presence or absence of various concentrations of TPOR agonist. Cell proliferation was assessed by the Cell Titer-Glo Luminescent Cell Viability Assay Kit (Promega) according to the manufacturer's instructions and luminescent signals were measured on a Victor 3 1420 Multilabel Counter (Perkin Elmer).

3. Signal Conversion Experiment

BaF3/MPL cells ($4 \times 10^5$ cells/ml) or human platelets were washed with PBS and serum-starved in RPMI-1640 medium containing 0.5% FBS overnight or 3 hours, respectively. Cells or platelets were stimulated with the indicated concentrations of TPOR agonist for the predetermined time period. Cells were lysed with RIPA (Radio Immunoprecipitation Assay) buffer (Elpis Biotech) supplemented with protease inhibitor cocktail (Calbiochem) and protein phosphatase inhibitor cocktail (Calbiochem). Lysates were quantified using the BCA assay kit (Pierce) and heated at 95° C. for 5 minutes in sodium dodecyl sulfate polyacrylamide gel electrophoresis (SDS-PAGE) sample buffer. Samples (10 μg/well) were separated on SDS-PAGE gels (Bio-Rad) and transferred to nitrocellulose membranes (Millipore). After sequential incubation with primary and secondary antibodies, chemiluminescent signals were detected using the Thermo ECL kit (Thermo Fisher Scientific) and then visualized with an Amersham Imager 600 (GE Healthcare Life Sciences). Janus family tyrosine kinase (Jak2), p-Jak2, signal transducer and activator of transcription (STAT5), p-STAT5 (Y925), STAT3, p-STAT3 (Y705), AKT, Primary antibody against p-AKT (S473), ERK and p-ERK1/2 (Thr202/Tyr204) were purchased from Cell Signaling Technology and antibodies against beta actin were purchased from Novus Biological.

4. Isolation of PB-CD34+ Cells

Aliquots of G-CSF mobilized human apheresis samples were obtained from healthy donors within the guidelines of standard procedures for hematopoietic progenitor cell apheresis at KUGH after written informed consent was obtained. Peripheral blood mononuclear cells (PBMC) were isolated by density gradient centrifugation using Ficolle-Hypaque (sigma) and immunoselection of PB-CD34+ cells was performed using the MACS CD34 MicroBead kit UltraPure (Miltenyi Biotec, Bergisch Gladbach, Germany)

according to the manufacturer's instructions. PB-CD34+ cell purity was typically higher than 95% by flow assay using CD34-PE.

5. Megakaryogenesis Assay Using Flow Cytometry

PB-CD34+ cells ($4 \times 10^4$/ml) were cultured in serum-free expansion medium (SFEM, Stem Cell Technologies) supplemented with 25 ng/ml rhSCF (PeproTech), 10 ng/ml rhIL6 (PeproTech), 10 ng/ml rhIL9 (PeproTech), 25 µg/ml LDL (Stem Cell Technologies) and various concentrations of TPOR agonists for up to 14 days. Half of the culture medium was replaced with fresh medium and cytokines every 3-4 days. Megakaryogenesis was assessed by detecting differentiation markers specific to megakaryocytes by flow cytometry. At each time point indicated, cells were harvested, washed with cold PBS, and labeled with CD41a-FITC (Miltenyi Biotec), CD42b-PE (Miltenyi Biotec) and 7-AAD (eBioscience) for 30 minutes at 4° C. in the dark. After washing, cells were analyzed using a CytoFlex flow cytometer (Beckman Coulter Inc.).

6. Megakaryocyte Ploidy Assay

PB-CD34+cells cultured for 13 days were labeled with CD41a-FITC for min at 4° C. and washed with cold PBS. The labeled cells were fixed by incubation with 1% paraformaldehyde for 15 minutes at room temperature. Cells were permeabilized with 70% methanol for 1 hour at −20° C. After permeabilization, the cells were treated with 10 µg/ml RNase (Roche), stained with 10 µg/ml propidium iodide (sigma) at room temperature for 30 minutes, and analyzed using a flow cytometer.

7. In Vivo Experiments

The effect of 2R13 on platelets and leukocytes (WBC) was confirmed in wild type (WT) and 5-fluorouracil (5-FU) induced thrombocytopenia mouse models. 2R13, recombinant human TPO (rHuTPO) was subcutaneously injected onto 8-10 week old BALB/c wild-type female mice (Nara Biotech, Seoul, Korea). 2R13 for single injection at concentrations of 5, 50, 100, and 500 µg/kg was injected. 2.5 µg/kg/day rHuTPO injection was used as a positive control for 7 days, and PBS containing BSA (PBS-BSA) was used as a negative control. To establish a thrombocytopenia model, 5-FU (Sigma, USA) was intraperitoneally injected into each group of mice at a dose of 150 mg/kg 1 hour before injection of 2R13 and rHuTPO. The concentration of 2R13 injected once was increased to 0.5 and 1 mg/kg. rHuTPO and PBS-BSA were injected at the same concentration for 7 days. Each mouse was anesthetized by intraperitoneal injection of ketamine (90 mg/kg) and xylazine (10 mg/kg), and 50 µl blood samples were taken in the retroorbital sinus using an ethylenediaminetetraacetic acid (EDTA) capillary tube (Marienfeld, Germany) every other day for 14 days (Day 0 before injection and Days 4, 7, 11 and 14 after treatment). Blood was transferred to EDTA tubes pre-filled with 450 µl of 2.5 mM EDTA buffer. Platelets and leukocytes were counted at the EONE Institute (Incheon, South Korea), and animal experiments were performed according to guidelines approved by the University College of Medicine Institutional Animal Care and Use Committee (2020-022).

8. Flow Cytometry

Mice were injected with 2R13 (0.5, 1 mg/kg/day) for 1 day, rHuTPO (2.5 µg/kg/day) and PBS-BSA for 7 days. On day 7, after the mice were sacrificed, the collected bone marrow cells (BM) were washed from the femur and tibia with PBS. BM red blood cells (RBCs) were lysed with lysis buffer for 1 min at room temperature. To examine the percentage of LSK cells, BM cells were suspended in PBS and incubated with PerCP-Cy5.5-labeled lineage antibodies, FITC-conjugated anti-Sca-1 and APC-conjugated anti-c-Kit antibodies for 4° C. for 30 minutes (BD, USA). Fluorescence was analyzed using a FACS Cantoll flow cytometer and FlowJo software (BD, USA).

<Example 1> Development of Functional Antibody That Specifically Activates TPOR Solution panning was performed as shown in FIG. 1A to find binding candidates for c-MPL in a naive human combinatorial Ab phage library (diversity: ~$10^9$). After 3 rounds of panning, it was confirmed that TPOR binding clones were clearly enriched and 6 clones with positive binding to TPOR were selected (FIG. 1B, FIG. 1C). Next, the presence of potential agonist antibodies was evaluated among these clones. After converting the selected clones into scFv-Fc fusion form, functional activity was investigated through TPO-dependent growth of chimeric cells (BaF3/MPL). Among the six clones, 2R13 showed the highest activity at a low concentration to select as the final candidate (FIG. 1D). An antibody ELISA was performed to characterize the binding affinity of 2R13 (FIG. 1E). The EC50 of 2R13 was 55.27 ng/ml. In addition, 2R13 was stained for BaF3/MPL in a concentration-dependent manner, whereas it was not stained for parental BaF3 cells, indicating specific binding to TPOR (FIG. 1F).

<Example 2> 2R13 Promoting Cell Proliferation and Stimulating TPOR Signaling Pathway in BaF3/MPL Cells To investigate the proliferative ability of 2R13, BaF3/MPL cells were cultured in the presence or absence of various concentrations of 2R13 or rhTPO. Both 2R13 and rhTPO promoted the growth of BaF3/MPL cells in a concentration-dependent manner (FIG. 2A). Relative cell proliferation was calculated as the maximum proliferative capacity of 100 ng/ml rhTPO. As a result, the EC50s of 2R13 and rhTPO were 53.4 ng/ml and 1.3 ng/ml, respectively. In parental BaF3 cells that do not express hMPL, cell proliferation increased only when treated with WEHI-CM containing mIL-3, but it was not increased when treated with 2R13 or rhTPO (FIG. 2B), which demonstrates that the increased cell proliferation displayed in FIG. 1A is specific to TPOR. The increased cell proliferation shown in, demonstrates that it is specific for TPOR. 2R13 and rhTPO also promoted the proliferation of MO7e cells known to express endogenous levels of TPOR (FIG. 2C). TPO binds to TPOR and triggers intracellular signaling including the JAK/STAT pathway. To confirm the mechanism by which 2R13 promotes cell proliferation in BaF3/MPL cells, the phosphorylation of JAK2, STAT5, STAT3, AKT and ERK was investigated. Similar to rhTPO, 2R13 increased the phosphorylation of JAK2, STAT5, STAT3, AKT and ERK in a concentration-dependent manner (FIG. 2D). In addition, 2R13 signaling was verified through the expression of a luciferase reporter gene mediated by STAT5 activation (FIG. 2E). Accordingly, it can be seen that 2R13 increases cell proliferation by stimulating phosphorylation of the JAK/STAT pathway together with the AKT and ERK pathways by binding to TPOR.

<Example 3> 2R13 Promoting Megakaryogenesis of PB-CD34+ Cells

Next, whether 2R13 could stimulate megakaryocyte formation in PB-CD34+ cells isolated from normal donors was investigated. PB-CD34+cells were cultured for 14 days in megakaryocytic differentiation medium in the absence or presence of 2R13 (50,300 and 1000 ng/ml) or 50 ng/ml rhTPO. Percentages of total and mature megakaryocytes were analyzed by flow cytometry for expression of CD41a and CD42b on days 4, 7, 11 and 14 (FIG. 3A). At day 11 of culture (representative flow cytometry plots are shown in FIG. 3B), total and megakaryocytic cell numbers were maximal in all conditions, and the percentage of CD41a+ cells was 56.4% at 50 ng/ml, 59.2% at 300 ng/ml and 59.6% at 1000 ng/ml 2R13 and 62.1% at 50 ng/ml rhTPO (FIG. 3C). The percentages of mature megakaryocytes (CD41a+ CD42b+ double positive) cells were 43.4% at 50 ng/ml, 44.7% at 300 ng/ml, 43.1% at 1000 ng/ml 2R13 and at 50 ng/ml rhTPO. Although there were no significant differences in % CD41a+ and % CD41a+CD42b+ between 2R13 and rhTPO, the total cell number was greater in the rhTPO treatment than in the 2R13 treatment. Accordingly, the number of CD41a+cells increased 5.7-fold at 50 ng/ml, 6.9-fold at 300 ng/ml, 7.9-fold at 1000 ng/ml 2R13, and 11.7-fold at 50 ng/ml rhTPO compared to the control group. The number of CD41a+CD42b+ cells increased 6.5-fold at 50 ng/ml, 7.7-fold at 300 ng/ml, 8.4-fold at 1000 ng/ml, and 12.5-fold at 50 ng/ml rhTPO compared to the control group. Similar results were obtained when PB-CD34+ cells from an additional donor were treated with 2R13 or TPO (FIG. 4 and FIG. 5).

<Example 4> 2R13 Increasing High Ploidy of Megakaryocytes

DNA ploidy of PB-CD34+ cells cultured for 13 days in megakaryocyte differentiation medium in the absence or presence of 2R13 (50,300 and 1000 ng/ml) or 50 ng/ml rhTPO was analyzed to confirm that these cells were mature megakaryocytes. The proportion of 2N megakaryocytes was 40.5% at 50 ng/ml, 43.9% at 300 ng/ml, 47.92% at 1000 ng/ml 2R13, and 54.6% at 50 ng/ml rhTPO (FIG. 6A). A representative histogram is shown in FIG. 6B. Cells treated with 2R13 had a higher percentage of megakaryocytes with 8N or greater than cells treated with rhTPO (FIG. 6C). Thus, 2R13 treated cells had a lower percentage of 2N megakaryocytes and higher ploidy than rhTPO. The number of next-high ploidy cells was 2.2 at 50 ng/ml, 2.3 at 300 ng/ml, 2.8 at 1000 ng/ml 2R13, and 4.9 at 50 ng/ml rhTPO. (≥8N) was calculated by multiplying the percentage of CD41a+ cells by the total number of cells (FIG. 6D). Thus, 2R13 did not increase the total cell number as much as rhTPO, but induced a higher percentage of ploidy megakaryocytic cells than rhTPO. Similar results were obtained when PB-CD34+ cells from additional donors treated with 2R13 or TPO (FIG. 7 and FIG. 8).

<Example 5> 2R13 Stimulating the TPOR Signaling Pathway in Human Platelets

As indicated above, 2R13 stimulated intracellular signaling pathways and cell proliferation in BaF3/MPL cells together with ectopic expression of TPOR. Whether 2R13 stimulates signaling pathways in primary human platelets was confirmed. Human platelets were serum starved for 3 hours and treated with 50, 300 and 1000 ng/ml 2R13 or 50 ng/ml rhTPO. Signal transduction induced by 2R13 was weaker than that induced by rhTPO, but 2R13 clearly phosphorylated JAK2, STAT5 and AKT in a concentration-dependent manner (FIG. 9A). In addition, platelets were treated with 300 ng/ml 2R13 and 50 ng/ml rhTPO for the indicated times up to 18 hours. 2R13 and rhTPO treatments maintained high levels of phosphorylation for a long period of time (0.25-18 h, FIG. 9B). Similar results were obtained when platelets from additional individuals treated with either 2R13 or TPO (FIG. 10).

<Example 6> 2R13 Capable of Increasing Platelet Count in WT Mouse Model with One Injection In the WT mouse model, the effect of 2R13 was evaluated by monitoring platelet and WBC levels in mice during and after the daily treatment period for 14 days (FIG. 11A). Mice received PBS-BSA as a negative control and rHuTPO as a positive control. Platelet and white blood cell counts were performed twice a week. It was found that the platelets of mice injected with 2R13 gradually increased in a dose-dependent manner from the 4th day and reached a peak on the 7th day (FIG. 11B). At each time point, the number of platelets of 2R13 injected once was relatively higher than that of rHuTPO 7-day injection. In all treatment groups, the number of platelets gradually decreased from day 11, and 5 µg/kg of 2R13 recovered to the pre-injection level on day 14. White blood cell counts appeared different from platelet counts (FIG. 11C). There was no significant change in the white blood cell count of mice injected with 2R13. On the 4th day after the injection, except for the high concentration of 2R13, the white blood cell count in the other treatment groups was lower than the normal value, and returned to the normal value on the 7th day. According to the above results, it can be seen that the effect of 2R13 in the WT mouse model is likely to be specific to platelets, but has little effect on WBC.

Next, it was confirmed whether 2R13 affects hematopoiesis in vivo. To this end, 2R13 (0.5, 1 mg/kg/day) was injected or 1 day and rHuTPO (2.5 µg/kg/day) and PBS-BSA were injected for 7 days. As a result, the number of LSK cells in the BM of the 2R13-treated group increased compared to that of the control group (FIG. 11D). This indicates that 2R13 can induce HSPC. Through the above WT mouse model experiments, it can be seen that the number of platelets obtained by one injection of 2R13 is superior to that of 7 days of rHuTPO injection, has hematopoietic function, and does not affect WBC.

<Example 7> 2R13 Capable of Preventing Thrombocytopenia in Mouse Model of Thrombocytopenia After the thrombocytopenia model induced by 5-FU, recovery of platelets was confirmed. 2R13 (0.5, 1 mg/kg) was injected once, rHuTPO (2.5 µg/kg/day), and PBS-BSA were subcutaneously injected into mice for 7 days, 1 hour before intraperitoneal injection of 5-FU 150 mg/kg (FIG. 12A). Another group of mice did not receive 5-FU treatment but still received PBS-BSA injections. Except for the control group, mice injected with 0.5 mg/kg of 2R13 had the lowest platelet count, and mice injected with 1 mg/kg had higher platelet counts than the positive control group and the normal group (FIG. 12B). From the 7th day, platelets in all treatment groups increased, and in particular, the 2R13 injection of 0.5 mg/kg reached the peak on the 10th day. The platelet count of mice injected with 1 mg/kg/day increased on day 7, but the platelet count was very similar to that of 2R13 injected with 0.5 mg/kg. The platelet count at day 10 was lower than that of 2R13 at 0.5 mg/kg. Although it is not difficult to find that the platelet count does not increase in a dose-dependent manner in 2R13, the effect of platelet increase compared to rHuTPO was clearly confirmed. Through this, the number of WBCs was confirmed (FIG. 12C), and since 2R13 still had no effect on leukocytes, it was clearly confirmed that the effect of 2R13 in vivo was specifically applied to platelets, but there was no change in leukocytes. In the thrombocytopenia model, it was also confirmed that 2R13 prevented thrombocytopenia at an earlier stage than normal and platelet recovery was superior to rHuTPO.

From the above description, those skilled in the art to which the present invention pertains will be able to understand that the present invention may be embodied in other specific forms without changing the technical spirit or essential characteristics thereof. In this regard, it should be understood that the embodiments described above are illustrative in all respects and not limiting. The scope of the present invention should be construed as including all changes or modifications derived from the meaning and scope of the claims to be described later and equivalent concepts rather than the detailed description above are included in the scope of the present invention.

The invention claimed is:

1. An anti-c-MPL antibody or antigen-binding fragment thereof, comprising:

a heavy chain variable region comprising a heavy chain CDR1 composed of amino acid sequence SEQ ID NO: 1, a heavy chain CDR2 composed of amino acid sequence SEQ ID NO: 2, and a heavy chain CDR3 composed of amino acid sequence SEQ ID NO: 3; and a light chain variable region comprising a light chain CDR1 composed of amino acid sequence SEQ ID NO: 4, a light chain CDR2 composed of amino acid sequence SEQ ID NO: 5, and a light chain CDR3 composed of amino acid sequence SEQ ID NO: 6.

2. A method for preventing or treating thrombocytopenia comprising administering a pharmaceutical composition comprising the anti-c-MPL antibody or antigen-binding fragment thereof of claim 1 as an active ingredient to a subject in need thereof.

3. The method for preventing or treating thrombocytopenia of claim 2, wherein the pharmaceutical composition induces generation of megakaryocytes, activation of platelets and an increase in platelet count.

4. A method for preventing or improving thrombocytopenia comprising administering a health functional food composition comprising the anti-c-MPL antibody or antigen-binding fragment thereof of claim 1 as an active ingredient to a subject in need thereof.

* * * * *